US010670589B2

(12) United States Patent
Van Herpen et al.

(10) Patent No.: US 10,670,589 B2
(45) Date of Patent: Jun. 2, 2020

(54) DETECTING TARGET MOLECULES IN A SAMPLE

(71) Applicant: KONINKLIJKE PHILIPS N.V., Eindhoven (NL)

(72) Inventors: Maarten Marinus Johannes Wilhelmus Van Herpen, Heesch (NL); Derk Jan Wilfred Klunder, Geldrop (NL); Hendrik Roelof Stapert, Rosmalen (NL)

(73) Assignee: Koninklijke Philips N.V., Eindhoven (NL)

( * ) Notice: Subject to any disclaimer, the term of this patent is extended or adjusted under 35 U.S.C. 154(b) by 191 days.

(21) Appl. No.: 15/710,887

(22) Filed: Sep. 21, 2017

(65) Prior Publication Data

US 2018/0074047 A1 Mar. 15, 2018

Related U.S. Application Data

(63) Continuation of application No. 12/446,461, filed as application No. PCT/IB2007/054266 on Oct. 19, 2007, now Pat. No. 10,101,321.

(30) Foreign Application Priority Data

Oct. 24, 2006 (EP) .................................... 06122797

(51) Int. Cl.
*C40B 60/04* (2006.01)
*G01N 33/53* (2006.01)
(Continued)

(52) U.S. Cl.
CPC ..... *G01N 33/5306* (2013.01); *G01N 21/6428* (2013.01); *C40B 30/10* (2013.01); *C40B 60/04* (2013.01)

(58) Field of Classification Search
None
See application file for complete search history.

(56) References Cited

U.S. PATENT DOCUMENTS 4,160,016 A 7/1979 Ullman
4,775,619 A 10/1988 Urdea
(Continued)

FOREIGN PATENT DOCUMENTS

EP 0153875 A2 9/1985
GB 2016687 A 9/1979
(Continued)

OTHER PUBLICATIONS

"Refractometry: Analyzing Results", Downloaded From http://www2.ups.edu/faculty/hanson/labtechniques/refractometry/interpret.htm on Jul. 29, 2016, pp. 1-4.
(Continued)

*Primary Examiner* — Christian C Boesen

(57) ABSTRACT

The invention relates to detection the presence of a target molecule in a sample, wherein the sample is contacted with a substrate, the substrate subsequently being washed in a wash step. In particular, the invention relates to a method of detecting the presence of a target molecule in a sample, the method comprising: (a) contacting the sample (37) with a substrate having immobilized thereon probe molecules that specifically binds to the target molecule; (b) washing the substrate (38) in a wash step by a wash fluid in order to remove or dilute unbound target molecules; (c) detect the presence of resultant binding complexes (39) on the substrate to determine whether the target molecule is present in the sample—The wash fluid being substantially refractive index matched to the substrate.

5 Claims, 4 Drawing Sheets

(51) Int. Cl.
*G01N 21/64* (2006.01)
*C40B 30/10* (2006.01)

(56) References Cited

U.S. PATENT DOCUMENTS

| | | |
|---|---|---|
| 4,882,288 A | 11/1989 | North |
| 5,807,756 A | 9/1998 | Bauman |
| 5,959,098 A | 9/1999 | Goldberg |
| 6,150,147 A | 11/2000 | Goldberg |
| 2002/0030810 A1 | 3/2002 | Gilby |
| 2003/0174992 A1 | 9/2003 | Levene |
| 2004/0175696 A1 | 9/2004 | Ullman |
| 2005/0048571 A1 | 3/2005 | Danielson |
| 2005/0266570 A1 | 12/2005 | Carey |
| 2008/0227188 A1 | 9/2008 | Wimberger-Friedl |

FOREIGN PATENT DOCUMENTS

| | | |
|---|---|---|
| JP | 61272659 A | 12/1986 |
| JP | 2004163257 A | 6/2004 |
| WO | 1993003347 A1 | 2/1993 |
| WO | 2007072415 A2 | 6/2007 |
| WO | 2007072418 A2 | 6/2007 |

OTHER PUBLICATIONS

Xie et al, "The Analysis of Antigen-Antibody Interactions on Protein Microarrays", Progress in Biochemistry and Biophysics, vol. 29, Issue 2, 2002, pp. 311-315 (English Abstract).

Shou et al, "Technique for Making High Quality Film Reflection Holograms", Journal of Xiamen University (Natural Science), Issue 2, 1999, p. 216-219 (English Abstract).

Garnsey et al (from Graft Transmissible Diseases of Citrus. Handbook for Detection and Diagnosis, 1991, International Organization of Citrus Virologists, Food and Agricultural Organization of the United Nations, Rome, 1991, 15 pages, accessed from http://www.fao.org/docrep/T0601E/To601E00.htm on Oct. 2, 2011).

Leis, et al (Optically Transparent Porous Medium for Nondestructive Studies of Microbial Biofilm Architecture and Transport Dynamics, 2005, Applied and Environmental Microbiology, vol. 71, pp. 4801-4808).

DETECTING TARGET MOLECULES IN A SAMPLE

CROSS REFERENCE TO RELATED APPLICATION

This application is a continuation of U.S. Ser. No. 12/446,461, filed on Apr. 21, 2009, which is the U.S. National Phase application under 35 U.S.C. § 371 of International Application No. PCT/IB2007/054266, filed on Oct. 19, 2007, which claims the benefit of European Patent Application No. 06122797.1, filed on Oct. 24, 2006. These applications are hereby incorporated by reference herein.

FIELD OF THE INVENTION

The invention relates to method of detecting the presence of a target molecule in a sample, and in particular to a method including contacting the sample with a substrate, the substrate subsequently being washed in a wash step. Moreover, the invention relates to an apparatus for preparing an assay, to an optical detection system for detecting a target molecule in an assay, to a substrate produced according to the method, and to a kit for performing an assay.

BACKGROUND OF THE INVENTION

Detection methods for particular biological molecules (bio-molecule) are manifold and many different approaches are presently available to the skilled person. The detection of specific biological molecules has a range of important practical applications, including gene identification for diagnostic purposes.

In general, the detection of biological specimen (the "target") such as polynucleotides, DNA, RNA, cells, and antibodies can especially be performed on an array for example a so-called bio-array (or micro-array) whereupon corresponding probe molecules are attached at various sites on the array. Target-probe examples include: DNA/RNA-oligonucleotide, antibody-antigen, cell-antibody/protein, hormone receptor-hormone, etc. When the target is bound or hybridized to a corresponding probe molecule, detection of the target bio-molecule may be performed by a variety of optical, electronic and even micromechanical methods.

A commonly used technique for detection of molecular binding on bio-arrays is optical detection of fluorescent labeled targets also known as a "label" or "marker". In general, a label may be any agent that is detectable with respect to its physical distribution and/or the intensity of the outgoing signal it gives. Fluorescent agents are widely used, but alternatives include phosphorescent agents, electroluminescent agents, chemiluminescent agents, bioluminescent agents, etc.

In general a problem of luminescence detection relates to separating the luminescent light with low intensity from the illuminating non-luminescent light, generally with high intensity. The reliability of luminescence detection therefore depends much on the optical characteristics of the spectral filters that are used in the separation process. The spectral filter function may include two steps: a first filter (called the 'excitation filter') preferably transmits the rays with a wavelength overlapping with the excitation spectrum of the label and blocks all rays with a wavelength that is inside the spectrum of the detection window. A second filter (called the 'emitter filter' or 'detection filter') preferably blocks all illumination light and transmits only the luminescent rays. The attenuation (blocking power) of a typical filter set is better than $10^{-6}$. To this end, also the optical properties of the substrate may be considered.

US 2005/0048571 discloses a substrate for reducing the auto-fluorescence in connection with optical detection from bio-arrays. In the disclosure, a porous layer of the substrate is tinted with a colorant agent. A drawback of the tinting of the substrate is however that it renders the substrate more expensive, and it may limit the number of different types of substrates that may be used.

The inventor of the present invention has appreciated that improved means for luminescence detection would be of benefit, and has in consequence devised the present invention.

SUMMARY OF THE INVENTION

The present invention seeks to provide an improved way of handling luminescence detection, such as in connection with performing a bio-assay, and preferably, the invention alleviates, mitigates or eliminates one or more of the above or other disadvantages singly or in any combination.

The invention is defined by the independent claims. The dependent claims define advantageous embodiments.

According to a first aspect of the present invention there is provided, a method of detecting the presence of a target molecule in a sample.

The target molecules may be bio-molecules conjugated to fluorophores.

Radiation is typically electromagnetic radiation in the visible or near-visible range, in the infrared (IR) or in the ultraviolet (UV) range.

In the context of the present invention, the term "fluorescence" and "phosphorescence" are to be understood in a broad sense as the emitted light resulting from a process where light has been absorbed at a certain wavelength by a molecule or atom, and subsequently emitted at the same or other wavelength after the lifetime of the excited molecule/atom in question. The emitted light is often, but need not be limited to, in the visible light spectrum (VIS), the UV spectrum, and the IR spectrum.

In an embodiment, the target molecules are detected by irradiating the substrate with a beam of radiation and subsequently detect the resulting luminescence beam from the substrate, i.e. the luminescence of the target molecules. The luminescence portion of detected radiation may photoluminescence, in particular fluorescence or phosphorescence.

The substrate for immobilizing probe molecules may be a bio-array arranged for analysis of biological targets. Typically, the bio-array may comprise a plurality of spots, wherein target molecules are immobilized. In this context, a spot is to be understood as an area having a certain extension. The spot may have a 2D or 3D configuration. The bio-array may comprise a silicon wafer, a glass plate, a porous membrane, such as nylon, nitro-cellulose, etc.

The optical properties of substrates used for immobilizing probe molecules may be such that the substrates have a very high reflectivity. The amount of scattering depends inter alia on the difference between the index of refraction of air and the substrate. Due to the high reflectivity, the incident radiation may have trouble to penetrate the substrate which reduces the amount of the incident radiation that is able to excite fluorophores that have bound to the substrate, especially within the substrate. Moreover, due to the high reflectivity, a large portion of the reflected light may in some configurations be reflected towards the detector.

The invention is particularly, but not exclusively, advantageous for reducing the reflectivity of the substrate. By using a substantially index matched fluid during a wash step, the reflectivity of the substrate can be greatly reduced. Moreover, the amount of light penetrating the substrate will be increased, leading to an improvement in the ratio of the incident radiation to the luminescence radiation.

In an advantageous embodiment, the refractive index of the wash fluid is within the range of the refractive index of the substrate plus/minus 10%. In principle, it is advantageous to obtain as good a match as possible of the refractive indexes, however a trade-off may be advantageous at least in situations where a specific type of wash fluid is required for given probe and/or target molecules and/or substrate. The match of the refractive index of the wash fluid relative to the refractive index of the substrate may be better than plus/minus 8%, plus/minus 6%, plus/minus 4%, plus/minus 2%.

In an advantageous embodiment, the wash fluid is an aqueous solution of sugar (sucrose) in water, where the weight percentage of sugar is between 50% to 80%. Aqueous solutions of sucrose may be advantageous since many fluorophore-conjugates dissolve easily in such a fluid.

Embodiments of the invention may advantageously be applied with a porous substrate, since a high reflection from the substrate may be even more problematic for porous substrates due to scattering of the pores.

In an embodiment of the method according to the invention the target molecules are bio-molecules conjugated to fluorophores.

In an embodiment of the method according to the invention the substrate is a bio-assay prepared with probe molecules, and the target molecules chemically bind to the probe molecules present in the substrate. In various advantageous embodiments, radiation pass filters, mirrors and possible other optical components may be introduced in the beam path from the radiation source to the detector.

For example the target molecules are detected by irradiating the substrate with a beam of radiation and subsequently detecting the resulting beam from the substrate.

The resulting beam may be transmitted through the substrate, or reflected from the substrate.

In an embodiment a first radiation pass filter (2) is introduced in the beam path between the radiation source (36) and the substrate (3, 30-32).

In an embodiment a second radiation pass filter (4) is introduced in the beam path between the substrate (3, 30-32) and the detector (35).

In an embodiment the beam path further comprises a dichroic mirror (5).

The method of the present invention may advantageously be at least partly automated, e.g. by implementing the method in an apparatus or a detection system in accordance with other aspects of the invention.

In a second aspect, the invention relates to an apparatus for preparing an assay.

In a third aspect, the invention relates to an optical detection system for detecting a target molecule in an assay.

The second and third aspects of the present invention may provide an apparatus and a detection system for detecting the presence, and optionally quantity, of one or more biological targets, i.e. target molecules in a sample. The system may detect targets that include, but are not limited to, polynucleotides, DNA, RNA, cells, and antibodies. Biological detection systems are often highly complicated and the present invention is advantageous in providing systems with a high reliability of the collected data.

In a fourth aspect, the invention relates to a substrate produced in accordance with the method of the first aspect.

In a fifth aspect, the invention relates to a kit for performing an assay.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIGS. 1A and 1B schematically illustrate two general embodiments of the optical setup.

DESCRIPTION OF EMBODIMENTS

In biological research and medical diagnostics many biomarkers are detected with the aid of an attached fluorescent label. The apparatus generally used is a fluorescent scanner or microscope, but for specific applications dedicated equipment is made based on the same detection principles.

Figure 1A:
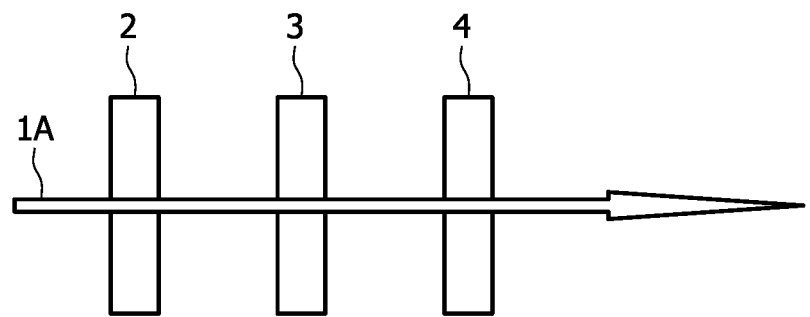
Figure 1B:
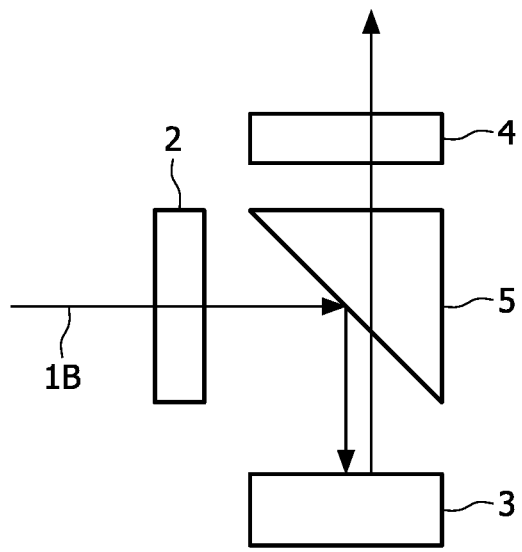

In a general embodiment of the present invention, an optical setup is used where at least two spectral filters are applied. FIG. 1 schematically illustrates two general embodiments. FIG. 1A shows a schematic illustration of a fluorescence detection device in a transmission mode where the resultant beam is transmitted through the substrate, whereas FIG. 1B shows a schematic illustration of a fluorescence detection device in a reflection mode where the resultant beam is reflected from the substrate. In FIGS. 1A and 1B a light beam 1A, 1B is emitted towards a substrate 3. In order to separate the resultant fluorescent light beam form the illuminating non-fluorescent light spectral filters are applied.

The spectral filter function consists of two steps: a first radiation filter 2 (called the 'excitation filter') being introduced in the beam path between the radiation (light) source and the substrate. The excitation filter preferably transmits the rays with a wavelength overlapping with the excitation spectrum of the label and blocks all rays with a wavelength that is inside the spectrum of the detection window. A second radiation filter 4 (called the 'emitter filter' or alternatively a 'detection filter') is introduced in the beam path, the emitter filter preferably blocks or at least substantially suppresses the illumination light and transmits only the fluorescent rays. The attenuation (blocking power) of a typical filter set is better than $10^{-6}$.

In FIG. 1B a beamsplitter 5 is moreover applied, the beamsplitter may e.g. be applied in a situation where the substrate is not transparent. In an alternative embodiment a dichroic mirror may be applied instead of a beamsplitter, a dichroic mirror reflects excitation light below a certain wavelength and transmits light above this wavelength. A dichroic mirror may therefore also act as an emitter filter 4, a separate emitter filter may still be used for increased performed, but it may not be necessary.

In an embodiment, the substrate may be illuminated by a number of high power LEDs, such as 2 to 10 red LEDs, a dark field setup may be applied. The resulting light being detected by a CCD camera (not shown) with the emitter filter mounted in front of the camera. As an example of a fluorophore, the dye Cy5 may be used.

The substrate 3 may be prepared in any suitable way of preparing a substrate, such as a bio-array substrate for use in a bio-assay. One typical array assay method involves immobilizing probe molecules in discrete locations on the substrate. A solution containing target molecules that bind with the attached probes is placed in contact with the bound probes under conditions sufficient to promote binding of targets in the solution to the complementary probes on the substrate to form a binding complex that is bound to the surface of the substrate. The bio-array may have a dimension in the micrometer range or even in the millimeter range. The number of different spots with distinct hybridization characteristics on the bio-array may vary from around 1 to 1000 per $mm^2$ on current arrays, and even higher, e.g. up to $10^6$ spots per $mm^2$. Within a spot on the array typically identical probe molecules are immobilized.

Figure 2:
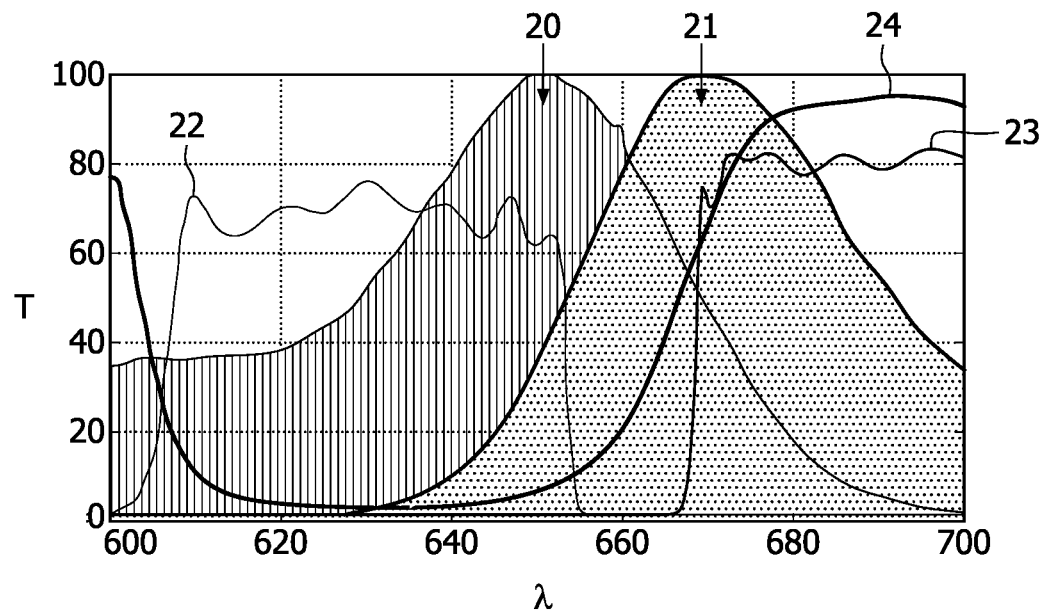
FIG. 2 illustrates spectral characteristics for the setup of FIG. 1B together with the spectra of the Cy5 dye.

FIG. 2 illustrates an embodiment of possible involved spectral characteristics for the setup of FIG. 1B together with the spectra of the Cy5 dye. FIG. 2 is generated by use of the Curv-o-matic online application, accessible from the Omega Optical website (www.omegafilters.com). FIG. 2 shows the transmission, T, in percent as a function of the wavelength, $\lambda$, in nanometers of the involved spectra, for the Omega filter set XF110-2.

FIG. 2 shows the excitation spectrum 20 of Cy5 having an excitation peak at 649 nm together with the corresponding emission spectrum 21 having an emission peak at 670 nm. The difference between illumination wavelength and fluorescent wavelength, per photon, is called the 'Stokes shift'. The Stokes shift of Cy5 is 21 nm.

The excitation filter is an Omega 630AF50 excitation filter exhibiting the spectrum denoted by 22 (bandwidth 50 nm, center at 630 nm). The emitter filter is an Omega 695AF55 emitter filter exhibiting the spectrum denoted by 23 (bandwidth 55 nm, center at 695 nm). The dichroic mirror is chosen so that the spectrum of the mirror, as denoted by 24, is such that it reflects incident light at the wavelength of the excitation radiation, whereas it transmits the resulting Stoke shifted light. The specific filter set and dichroic mirror are provided as an example, and may not necessarily be applied in a all embodiments. For example, as mentioned in connection with FIG. 1B, an emitter filter may be dispensed when using a dichroic mirror.

Table 1 shows the results of an experiment, in which the optical properties were measured of porous Nylon substrates (Nytran N and Nytran SPC) 3. The experiment was performed by irradiating the substrate at the incident wavelength of 650 nm and subsequently detecting the resulting beam from the substrate. Two types of experiments were performed, one with a dry substrate, and one which have been exposed to water in a wash step.

TABLE 1

|  | Wet | Dry |
|---|---|---|
| Nytran N |  |  |
| Transmittance | 31.1% | 4.2% |
| Reflectance | 68.7% | 95.3% |
| Absorbance | 0.1% | 0.5% |

TABLE 1-continued

|  | Wet | Dry |
|---|---|---|
| Nytran SPC |  |  |
| Transmittance | 33.8% | 5.3% |
| Reflectance | 65.4% | 94.4% |
| Absorbance | 0.8% | 0.4% |

As can be seen in Table 1, the substrate has a very high reflectivity, especially when dry. The cause for this high reflectivity is scattering due to the high porosity of the substrate. The amount of scattering depends on the difference between the index of refraction of air and substrate. Compared to air, the index of water is much closer to the index of the substrate. This is the reason why a wet substrate has a lower reflection than a dry substrate.

In accordance with the present invention, a substantially index matching fluid is applied during the wash step of the assay, and thereby the reflectivity of the substrate can be greatly reduced, down to a typical value of 5% reflectivity.

The improvement in excitation intensity may be at least factor of 3 as compared to water as the washing fluid, but can be as high as 20 compared to a dry substrate.

The improvement in the ratio of excitation and fluorescence radiation may be at least 14 as compared to water and can be as high as 19 as compared to a dry substrate.

Figure 3A:
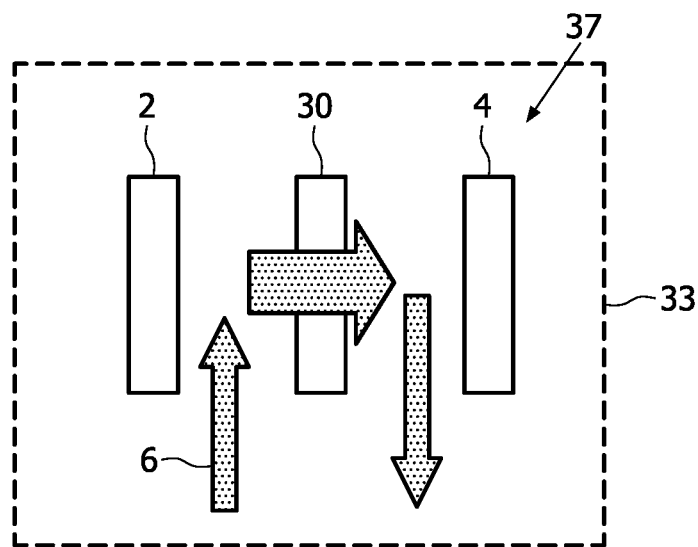
FIGS. 3A, 3B and 3C illustrate an embodiment of a method of detecting the presence of a target molecule in a sample.
Figure 3B:
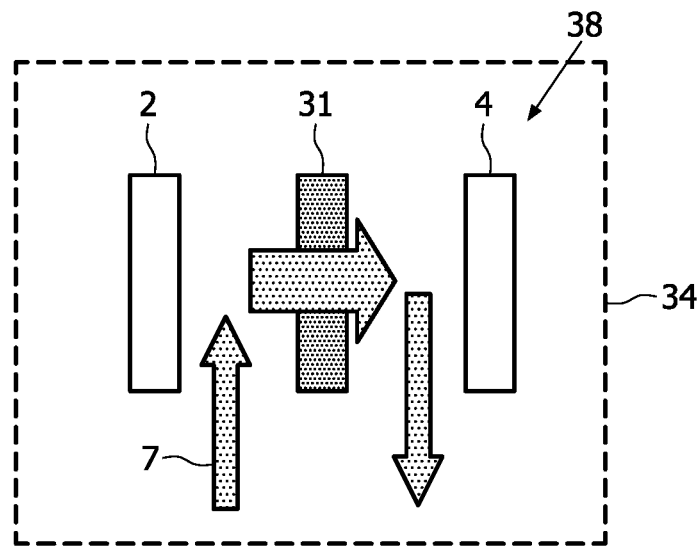
Figure 3C:
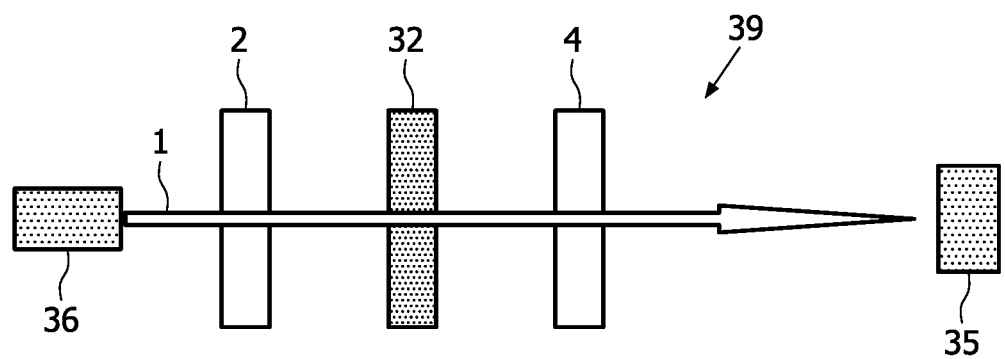

FIG. 3 illustrates an embodiment of a method of detecting the presence of a target molecule in a sample in accordance with the present invention, where a bio-array is prepared using as a wash-step. FIG. 3A to 3C illustrates at least some of the involved steps.

In steps prior to the step of FIG. 3A, a sample fluid has been prepared with target bio-molecules conjugated to fluorophores. In the step 37 of FIG. 3A the sample 6 is contacted with the substrate 30 by flowing the sample fluid through the substrate 30, causing the target bio-molecules with fluorophores to attach to specific binding locations on the substrate. It is to be understood that target molecules may be contacted to the substrate in alternative ways, e.g. by the application of drop deposition from pulsejets, or by other suitable means.

During the preparation steps not all fluorophores can be expected to bind to a probe molecule. This means that in addition to fluorophores that have bound to the substrate 30, there are also unbound fluorophores that are not attached to the substrate, but are still present. A wash step 38 is applied to remove or at least dilute any unbound fluorophore-conjugates, leaving only bound fluorophore-conjugates behind on the substrate, as illustrated in FIG. 3B. During this step a washing liquid 7 is pressed through the substrate 31. In the current invention, the washing liquid 7 is chosen such, that it has the index of refraction of the wash fluid substantially match the index of refraction of the substrate 31.

FIG. 3C illustrate a detection step 39 in order to detect the presence of resultant binding complexes on the substrate, the detection step has been described in connection with FIG. 1. Because a substantially index matching fluid was used during the washing step (FIG. 3B), the reflectivity of the substrate 32 has been reduced considerably, improving the sensitivity of the detection step. The detection is typically applied in direct continuation of the wash step so that the substrate is still wet.

In different embodiments of the present invention different index matching fluids that can be used. In one embodiment an oils may be used, as an example of a suitable oil; Zeiss Immersol 518F, with n=1.518 at 23° C. may be used.

Figure 4:
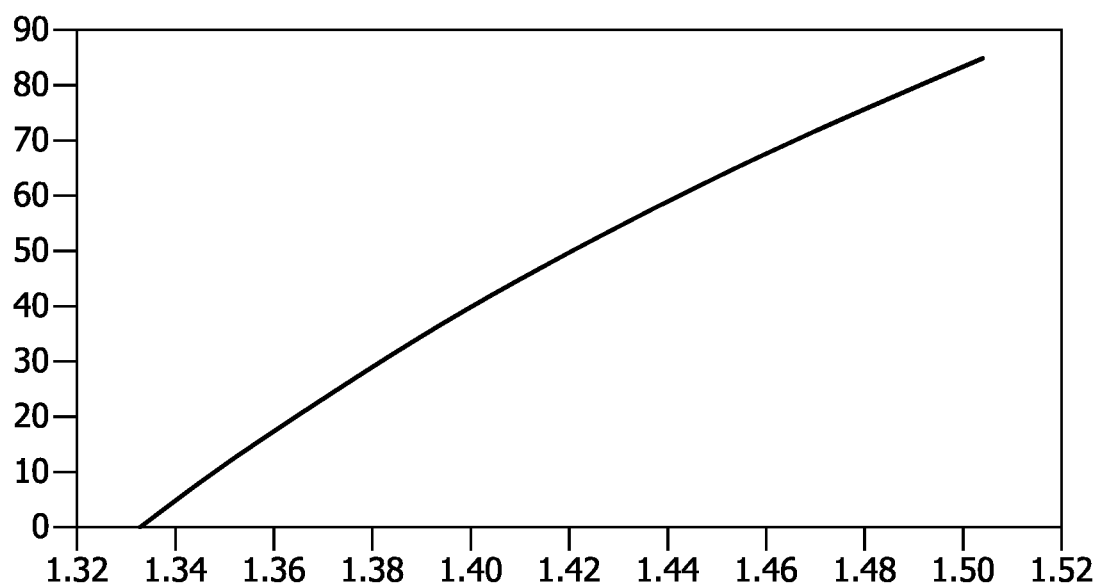
FIG. 4 shows a graph of the index of refraction, n, of aqueous sucrose solutions, as a function of the weight percent, p.

In other embodiments, aqueous solutions of dense materials may be applied. In a specific embodiment an aqueous solution of sugar is used. It may be advantageous to use a solution of 60% to 70% sugar (sucrose, etc.), thereby achieving an index of refraction of 1.45 (see FIG. 4 illustrating the index of refraction, n, of aqueous sucrose solutions, as a function of the weight percent, p). Aqueous sucrose solutions may be a preferred index matching fluid, because fluorophore-conjugates dissolve easily in such a fluid, making the fluid suitable for both the washing step and the detection step.

It is to be understood that in alternative embodiment, additional washing steps may be applied. Such additional washing steps may be applied with different of same wash fluids, in the situation were different wash fluids are used for different wash steps, at least the last wash step is conducted using a wash fluid being substantially refractive index matched to the substrate.

The steps of FIG. 3 and possible additional steps may be performed, possibly in an automated or semi-automated manner, in an apparatus for preparing an assay and/or an optical detection system. Such apparatuses and systems may include a handling unit 33 for receiving a substrate, and a wash unit 34 for performing a wash step on the substrate. The handling unit and the wash unit may be embodied in the same unit, or the sample may be moved between units. Embodiments of optical detection systems also comprise a radiation source 36 such as one or more laser diodes and a radiation detector 35, such as a CCD.

Kits for use in target detection assays are also provided. The kits at least include a wash fluid, the wash fluid being substantially index matched to a substrate and instructions for using the wash fluid. The kits may further include one or more additional components to be used when carrying out a target detection assay, such as one or more substrates, sample preparation reagents, buffers, labels, etc. The instructions for use may be provided in paper format, be recorded on a suitable recording medium, be provided in the form of directions as how to access the instructions via a remote source, e.g. the Internet, etc.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. An apparatus for preparing an assay, the apparatus comprising:
    a handler
    arranged to receive a substrate,
        wherein the substrate has a first side and a second side,
        wherein the second side is opposite to the first side,
        wherein probe molecules are immobilized upon the substrate,
        wherein the probe molecules specifically bind to a target molecule, and
        wherein the handler is arranged to contact a sample with the substrate; and
    a washer
    arranged to press a wash fluid through the substrate by introducing a stream of the wash fluid under pressure at the first side of the substrate, the stream of the wash fluid passing through the substrate and out of the second side of the substrate, and
        wherein the wash fluid has a refractive index substantially matched to a refractive index of the substrate.

2. The apparatus of claim 1, wherein the refractive index of the wash fluid is within a range of the refractive index of the substrate, and
    wherein the range is a range of plus and minus 10% to the refractive index of the substrate.

3. The apparatus of claim 1, wherein the handler is arranged to flow the sample through the substrate by introducing a stream of the sample to the first side of the substrate, the stream of the sample passing through and out of the second side of the substrate forming binding complexes that are bound throughout the substrate while leaving unbound luminescently labeled target molecules.

4. An apparatus for preparing an assay, the apparatus comprising:
    a handler arranged to receive a substrate, the substrate having probe molecules immobilized thereon, the probe molecules specifically bind to a target molecule,
    wherein the substrate has a first side and a second side,
    wherein the second side is opposite to the first side,
    wherein the handler is arranged to contact a sample with the substrate,
    wherein the handler is arranged to flow the sample through the substrate by introducing a stream of the sample to the first side of the substrate, the stream of the sample passing through and out of the second side of the substrate forming binding complexes that are bound throughout the substrate while leaving unbound luminescently labeled target molecules; and
    a washer arranged to perform washing on the substrate using a wash fluid, the wash fluid having a refractive index substantially matched to a refractive index of the substrate.

5. The apparatus of claim 4, wherein the refractive index of the wash fluid is within a range of the refractive index of the substrate, and
    wherein the range is a range of plus and minus 10% to the refractive index of the substrate.

* * * * *